(12) United States Patent
Gumennik et al.

(10) Patent No.: US 11,629,325 B2
(45) Date of Patent: Apr. 18, 2023

(54) TROPHOWELL

(71) Applicant: The Trustees of Indiana University, Indianapolis, IN (US)

(72) Inventors: Alexander Gumennik, Bloomington, IN (US); Louis Alexandre van der Elst, Bloomington, IN (US); Merve Gokce Kurtoglu, Bloomington, IN (US)

(73) Assignee: The Trustees of Indiana University, Indianapolis, IN (US)

( * ) Notice: Subject to any disclaimer, the term of this patent is extended or adjusted under 35 U.S.C. 154(b) by 449 days.

(21) Appl. No.: 16/834,572

(22) Filed: Mar. 30, 2020

(65) Prior Publication Data

US 2021/0301244 A1 Sep. 30, 2021

(51) Int. Cl.
*C12M 1/34* (2006.01)
*C12M 1/12* (2006.01)
*C12M 1/32* (2006.01)
*G01N 33/50* (2006.01)

(52) U.S. Cl.
CPC ............ *C12M 41/00* (2013.01); *C12M 23/06* (2013.01); *C12M 23/12* (2013.01); *C12M 25/00* (2013.01); *G01N 33/5044* (2013.01)

(58) Field of Classification Search
CPC ...... C12M 41/00; C12M 41/36; C12M 35/08; C12M 25/00; C12M 23/06; C12M 23/12; G01N 33/5044; G01N 33/5008
See application file for complete search history.

(56) References Cited

U.S. PATENT DOCUMENTS

| | | | | |
|---|---|---|---|---|
| 7,846,717 | B2* | 12/2010 | Yasuda | C12M 25/02 |
| | | | | 435/287.7 |
| 2004/0126876 | A1* | 7/2004 | Ravin | G02B 21/34 |
| | | | | 359/398 |
| 2018/0066220 | A1* | 3/2018 | Nath | C12M 33/12 |
| 2018/0320122 | A1* | 11/2018 | Blanchard | C12M 23/50 |

OTHER PUBLICATIONS

Berthiaume, François, Timothy J. Maguire, and Martin L. Yarmush. "Tissue Engineering and Regenerative Medicine: History, Progress, and Challenges." Annual Review of Chemical and Biomolecular Engineering 2, pp. 403-430 (2011).
Christian Frantz, Kathleen M. Stewart, and Valerie M. Weaver. "The extracellular matrix at a glance." Journal of Cell Science 123, pp. 4195-4200 (2010).
Park, Kyung Min, Sharon Gerecht. "Harnessing developmental processes for vascular engineering and regeneration." Development for Advances in Developmental Biology and Stem Cells 141.14, pp. 2760-2769 (2014).

(Continued)

*Primary Examiner* — Michael L Hobbs
(74) *Attorney, Agent, or Firm* — Barnes & Thornburg LLP

(57) ABSTRACT

A platform for testing cell response to biochemical agents. The TrophoWell™ includes a well which contains a gel, and a plurality of capillaries that open into it. Cells and various biochemical agents such as drugs and growth factors are flown through those capillaries. The platform allows for the evaluation of cell response by imaging. The platform is a cost effective testing platform and can be used in the fields for drug discovery and personalized medicine.

6 Claims, 14 Drawing Sheets

(56) References Cited

OTHER PUBLICATIONS

Formlabs, "3D Printing Splints with Formlabs SLA Printers," Feb. 2020, Formlabs.com., pp. 1-16; downloaded Jun. 26, 2020.
Dental SG Safety Data Sheet provided by Formlabs describing the contents of Dental SG; Issued Jan. 5, 2018, pp. 1-9.
Charan, Jaykaran, and N. D. Kantharia. "How to calculate sample size in animal studies?" Journal of Pharmacology 4.4, pp. 303-306 (2013).
Bekusova, Victoriia, Vasily Patsanovskii, Alexander D. Nozdrachev, Alexandr P. Trashkov, Margarita R. Artemenko, and Vladimir N Anisimov. "Metformin prevents hormonal and metabolic disturbances and 1,2-dimethylhydrazine-induced colon carcinogenesis in non-diabetic rats." Cancer Biology and Medicine 14.1 (2017).
Lovell-Badge, Robin. "Nine out of ten statistics are taken out of context." Understanding Animal Research (2013).
Fauber, John. "Kalydeco: A Price Too High to Pay?" MedPage Today (2013). Accessed online Jun. 26, 2020, https://www.medpagetoday.com/pulmonology/cysticfibrosis/42018 and provided as hardcopy pp. 1-6.

* cited by examiner

TROPHOWELL

BACKGROUND

Although regenerative medicine, bioprinting, and microfluidic lab-on-chips are expanding fields of research, the fusion of the three at the macroscale level has been limited. The development of experimental tools in this sphere can have positive repercussion in many areas of medicine. Two such areas of impact are outlined below.

First, it would have a positive impact in the field of drug discovery. The use of animals in preclinical studies is widespread in medical research. For early phase research, 6-10 animals are typically used per treatment. During the process of drug development, the chemical composition and dosage are critical variables, and thus, a range of these variables need to be evaluated. During long-term testing of new drugs, the gold standard is 50 animals per group, 2 sexes, 2 to 3 doses, and 2 species (e.g. rats and mice)[11].

A primary objective in the field of clinical research, as outlined in a study discussing the misuse of statistics in clinical research[12], is to limit the usage of animal studies to appropriately designed experiments, especially considering that an 88% drug failure rate is recorded. Although this study underlines the importance of animal research, it also serves to bring to attention the extensive use of animals during the drug development process. There is also the additional burden of having to feed and maintain the animals for an extensive period of time during the experimentation period. Thus, there is a need for an alternative to animal studies during early-stage drug research.

Second, it would significantly affect the field of personalized medicine. Human biology is very complex and the biological make-up of each person varies significantly. Hence, technological developments in health are beginning to gravitate toward patient-specific treatments. For instance, cancer cells of the same cancer type differ from patient to patient. Also, drugs with the same ingredients and concentrations affect patients differently. Personalized or precision medicine is also being targeted in the realm of genetic engineering. Personalized medicine is a patient-based treatment method which determines a patient's biological response by collecting and analyzing their genetic data and designing treatments most conducive to that specific patient. This optimizes the recovery rate for each individual and prevents unaccounted harmful side-effects.

Furthermore, personalized treatment is still very expensive, and is thus, inaccessible to many patients. Cost reduction over the last several years has been marginal. Kalydeco® (ivacaftor), a special drug for cystic fibrosis, has an annual cost of about $300.000 per patient[14]. Gleevec® (imatinib mesylate), a targeted cancer drug, costs has an annual cost of about $146.000 per individual patient[15]. It is anticipated that the Precision Initiative Medicine research endeavor established by U.S. government in collaboration with the National Institute of Health's (NIH) effort to improve personalized medicine technology[16] will integrate a solution to alleviate such unaffordable costs. However, for the present time, this work is targeted towards mass data collection, with the NIH All of Us research program collaborating with millions of people to create a genetic data pool to understand the biological mechanisms better[18].

Most of the devices used in these two fields rely on microfluidic chip development. There are several drawbacks of microfluidic chip technology. Fabrication of microfluidic chips requires complex lithography design and different coating methods which need be performed in a cleanroom environment. Users need to undergo a training to use microfluidic chips accurately in case of complicated structure. In addition, their chip production comes with higher costs, expensive lab setup, longer production time, and hazardous material manipulation. Since macroscale bioactivities are intertwined with microscale bioactivities, the TrophoWell™ is unique in allowing for the observance of both simultaneously.

DETAILED DESCRIPTION OF DRAWINGS

Definitions

Figure 1:
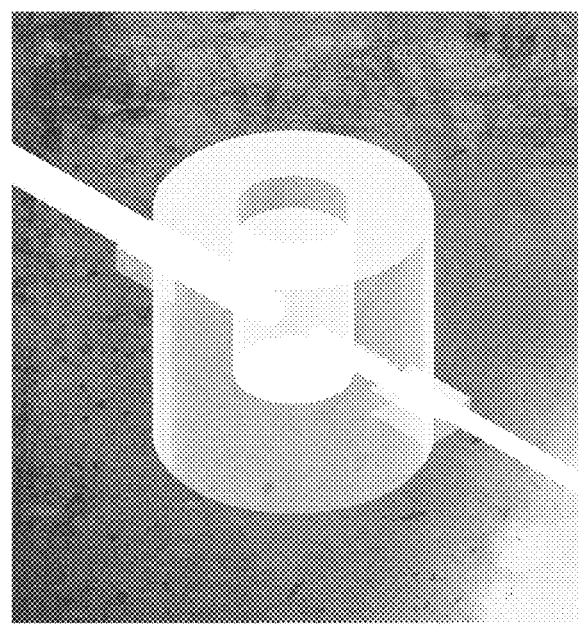
FIG. 1 illustrates a computer-aided design of a TrophoWell™ for testing the diffusion and interaction of two agents in specific media.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

Each of the terms "about" and "approximately," as used herein, mean greater or lesser than the value or range of values stated by 10 percent, but is not intended to designate any value or range of values to only this broader definition. Each value or range of values preceded by the term "about" or the term "approximately" also is intended to encompass the embodiment of the stated absolute value or range of values.

As used herein, the terms "including," "containing," and "comprising" are used in their open, non-limiting sense.

As used herein, the term "engineered" may mean "bio-engineered" when used in the context of one or more biological materials.

As used herein, the term "real tissue" may mean tissue produced in vivo by a living, multicellular organism in contrast to "engineered tissue" or "bioengineered tissue."

As used herein, the term "bioprinting" may mean additive manufacturing of three-dimensional biocompatible and living structures, such as tissue.

As used herein, the term "autoclaved" may mean reusable equipment has been sterilized in a pressurized chamber at highly elevated temperatures (121° C./249° F.).

As used herein, the term "additive manufacturing" may mean a method used to build three-dimensional objects or products, typically layer-by-layer.

As used herein, the term "assay" may mean a qualitative measurement of the content of a specific compound or agent in a microenvironment.

As used herein, the term "bioink" may mean a hydrogel containing cells.

As used herein, the term "a biocompatible material" may mean a material or chemical interacting with living biology is compatible if it does not initiate immune responses, damage or degrade structural properties, and is hazardous or infectious.

As used herein, the term "biomaterial" may mean a biocompatible materials that can be degradable or simply interact in an inert way with a biological environment, in the form of biopolymers, bioceramics, or metals.

As used herein, the term "extracellular matrix" may mean a structural network surrounding cells in animals and plants, naturally made of proteins, growth factors, and more. Synthetic ones can be made of solvents, hydrogels, biopolymers, aerogels, foams (traditionally porous structures).

As used herein, the term "growth factors" may mean a biochemical signal stimulating the growth, differentiation, or specific behavior of cells, such as vitamins or hormones.

As used herein, the term "hydrogel" may mean biocompatible polymer gel providing suspension and structure to cells.

As used herein, the term "lab-on-chips" may mean polymer biocompatible device made of microfluidic channels seeking to integrate separate traditional lab processes all-in-one on a chip.

As used herein, the term "microfluidics" may mean science of manipulating fluidics at the micro- and nano-scale.

As used herein, the term "regenerative medicine" may mean a remedy involving replacing or regenerating human cells, tissue or organs, typically through transplantation.

As used herein, the term "stem cell" may mean stem cells have the potential to differentiate (develop) into many different types of cells along with a high regenerative qualities. They are an essential building block to regenerative medicine.

As used herein, the term "tissue engineering" may mean development of viable tissue for transplantation as a solution in regenerative medicine.

As used herein, the abbreviation "FAMES Lab" means "Fibers and Additive Manufacturing Enabled Systems Laboratory."

As used herein, the abbreviation "VEGF" means "Vascular Endothelial Growth Factor."

As used herein, the abbreviation "CAD" means "Computer-Aided Design."

As used herein, "TrophoWell™" is testing device with an enclosure containing a gel, and multiple capillaries which open into that enclosure. Cells and biochemical agents maybe flown through those capillaries.

EMBODIMENTS

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

The invention described in the current disclosure uses state-of-the-art contemporary bioengineering and outperforms similar lab-on-chips solutions and can be used for both drug development applications, and, as a tool for designing and testing personalized medicines. The TrophoWell™ is a personalizable three-dimensional petri dish. It is device that has ubiquitous applications, and can be modified based on those applications. It can be used as an early-stage testing platform for drugs, chemicals, or other biological agents that affect the human body. Additionally, the device can be used as a platform for tissue engineering—a process replicates realistic and viable human tissue outside of the body using both natural and synthetic materials[1]. The device allows for the testing of biochemical and physical reactions for medical purposes personalized to specific patients. TrophoWell™ is easy to use, easy to process, portable and disposable.

Figure 2:
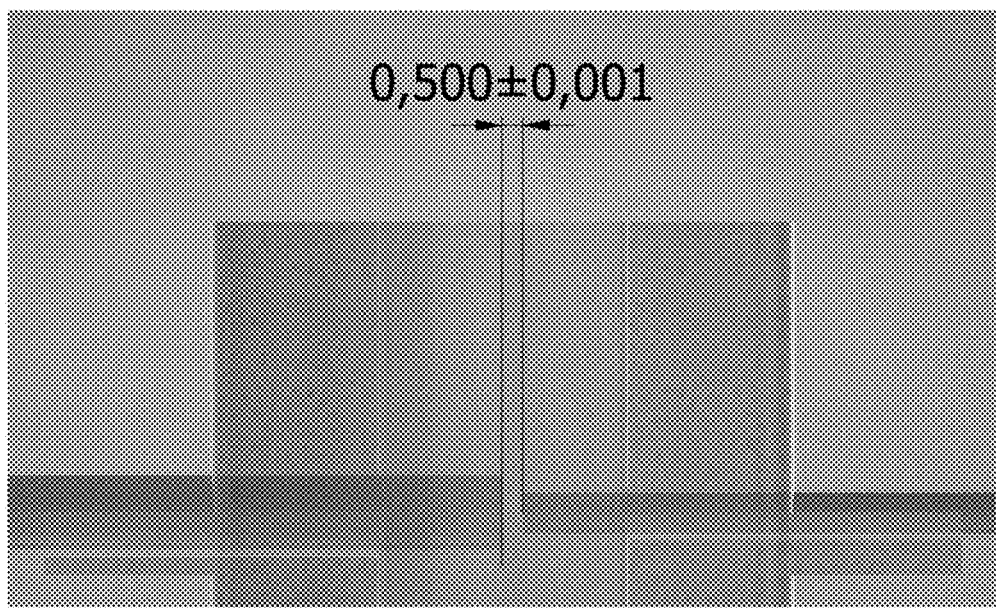
FIG. 2 depicts an adjustable distance between two capillaries that provide interacting agents.

As shown in FIG. 1, in one embodiment, the TrophoWell™ is a well containing extracellular matrix (ECM), in which two capillaries feed two different agents. As illustrated in FIG. 2, the distance between the outlets of the two capillaries can be adjusted based on the interaction distance required for the experiment. The well is made of biocompatible dental resin, clear for optical tests[3], and autoclavable[4] for reuse in a biosafety cabinet. Should the specific need be, use of specific resins allows the device to be sterilized by autoclave and therefore renders it reusable, meeting not only biomedical but also ecological standards.

Figure 3:
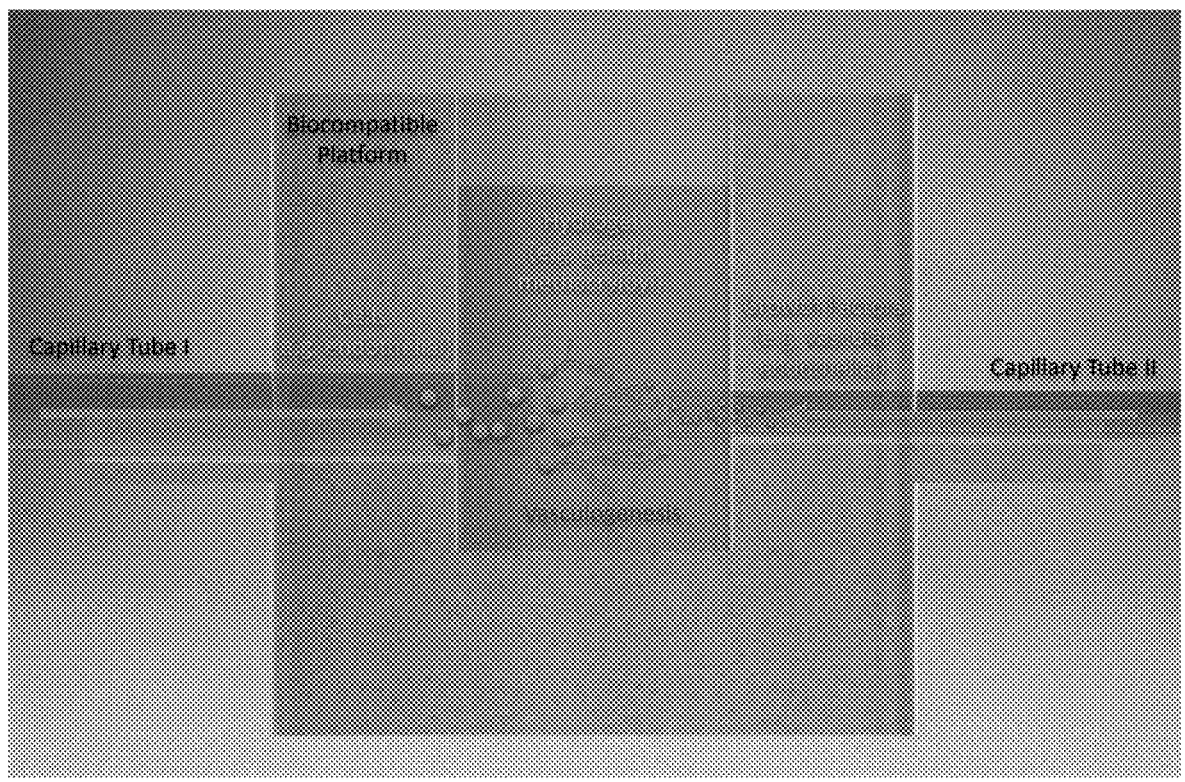
FIG. 3 illustrates usage of the TrophoWell™ for initiating and observing microvasculature growth.

The device welcomes adaptable complexity through parametric CAD, depending on the indication of use. To illustrate further context, FIG. 3 shows a possible application of the device. The device is used to grow microvasculature in a hydrogel based of previously conducted experiments[5].

Here, the VEGF signals the endothelial cells to form a microvasculature network. This method allows the irrigation of nutrients throughout the hydrogel making the structure more viable for a tissue application. Another embodiment of this device could integrate a neural network, allow for the growth of glands, and incline the appropriate personalized stem cells to make realistic skin. In the aftermath of the development of such 'personalized' skin, treatments could be performed on that skin in order to observe the impact of different drugs on that specific patient.

The technology underlying this platform utilizes capillary flow effect involving the first capillary tube which has cells in appropriate growth media, and the selected growth factor, to create a microenvironment suitable for vascularization with applicable fluid flow and the support of bioink. Bioprinting techniques can provide differentiation cues to the cells. For example, a specific structure of ECM can be printed by the bioprinter to provide suspension. One of the capillaries can provide growth media to the cells, while the other capillary can provide the signaling molecules that will initiate the cells response.

Figure 4A:
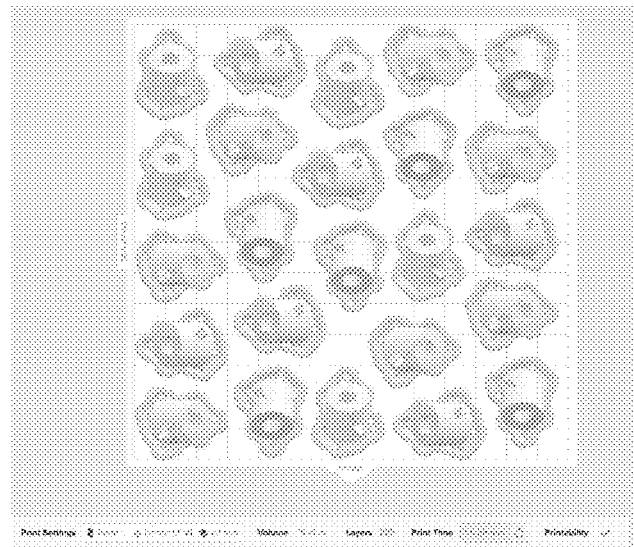
FIG. 4A shows the built platform enabling the simultaneous printing of 24 TrophoWell™.
Figure 4B:
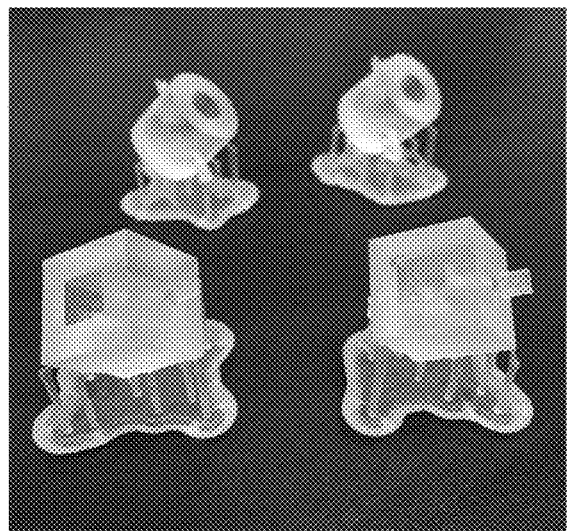
FIG. 4B illustrates cylindrical and cubic TrophoWell™ printed by Steriolitography 3D printing.

The TrophoWell™ is a new testing platform which is printed from the biocompatible dental resin by stereolithography technique. A Form $2^7$ stereolithography printer can be used to print biocompatible and autoclavable components, and a Bio $X^8$ bioprinter can be used for printing biomaterials. A Form 2 stereolithography printer can be used to create models for diverse personalized test benches. Design of the model is prepared CAD, and specific spatial arrangements are made by the software program of the device. Stereolithography technique allows the production of multiple TrophoWell™ in a few hours. The printing process of creating a TrophoWell™ takes about two hours, and 24 TrophoWell™ can be created in that time, as illustrated in FIG. 4. Hence, this platform lends itself well to mass production. Current platforms for testing drugs can be found in the form of lab-on-chips microfluidics devices, operating on a microscale, or in the form of well plates and bioreactors, operating on a macroscale. The TrophoWell™ allows for work at the macroscale while allowing for observation of life at low Reynold's number.

In some embodiments, the TrophoWell™ may have multiple inlets, outlets, and chamber. Due to the additive manufacturing nature of the TrophoWell™, it does not have specific constraints regarding the number of inlets, outlets, chambers. Thus, the TrophoWell™ may have any number of inlets, outlets, and chambers. There is an optical guide through the experimental chamber of the device for observation purposes. Observations may be done under a microscope. The main chamber is typically filled with an extracellular matrix material dependent on the type of cells used. An artifact, such as a tumor, blood clutter, or kidney stone may also be inserted through the chamber for testing purposes. The inlets can provide any fluid or gas. This may include, but is not limited to nutrition media, cells, growth factors, biochemical, or drugs. The experimentation assays may include, but are not limited to, evaluation of vascular growth, evaluation of neural growth, cancer development observations, evaluation of allergic reactions, toxicology studies, and drug release studies.

Figure 6:
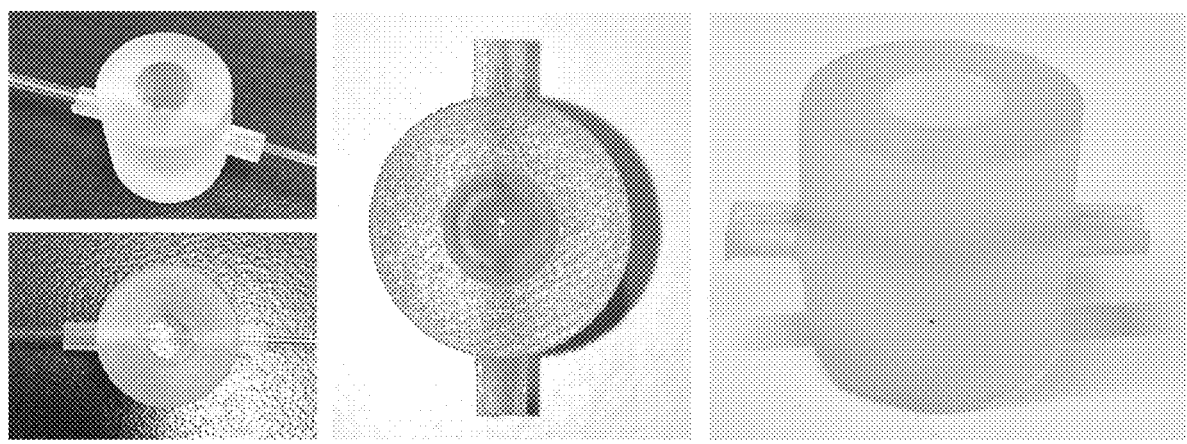
FIG. 6 shows printed TrophoWell™ design with capillary tubes as inlets for the biochemicals and cells represented here by a blue and yellow dye.
Figure 7:
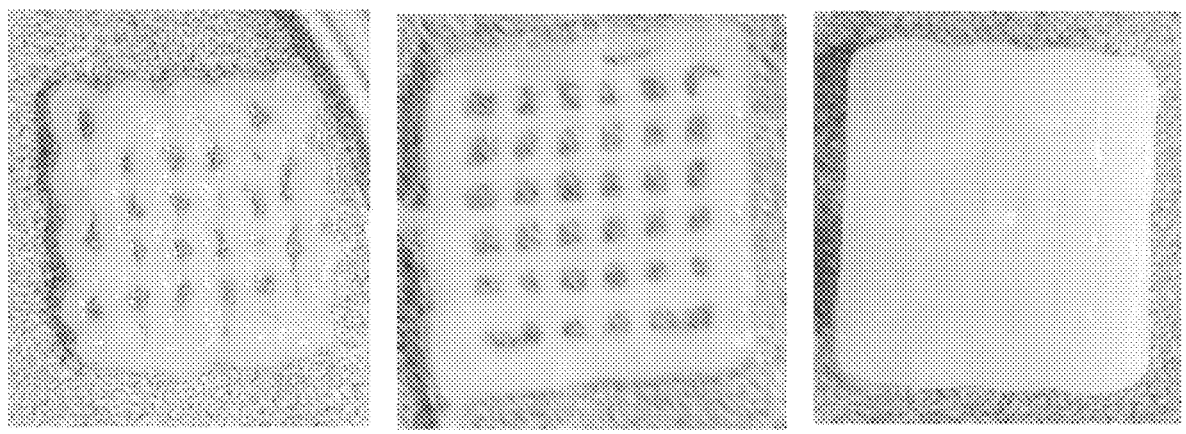
FIG. 7 illustrates preliminary tests of bioprinting and infill densities.

FIG. 6 illustrates one embodiment of the TrophoWell™ where gelatin methacrylate is used as the extracellular matrix. The TrophoWell™ is made of clear dental resin and the capillaries have different sizes (1.8 OD and 1.0 OD) adapted to the agents that are flown through them. The distance between the capillaries is varied from about 200 microns to about 500 microns to examine interactions at different distances.

A simulation of the chemotaxis of Human Umbilical Vein Endothelial Cells (HUVEC) towards growth factors is used to evaluate cell behavior. This model includes contact modulated interactions between cells and media, chemotaxis of HUVEC cells depending growth factor (such as VEGF), and the diffusion of growth factors though a gel-based extracellular matrix with a certain diffusion coefficient and diffusion length. It should be noted, that the cells also secrete growth factor themselves at a low secretion rate while they respond to the VEGF that is externally supplied.

Figure 5:
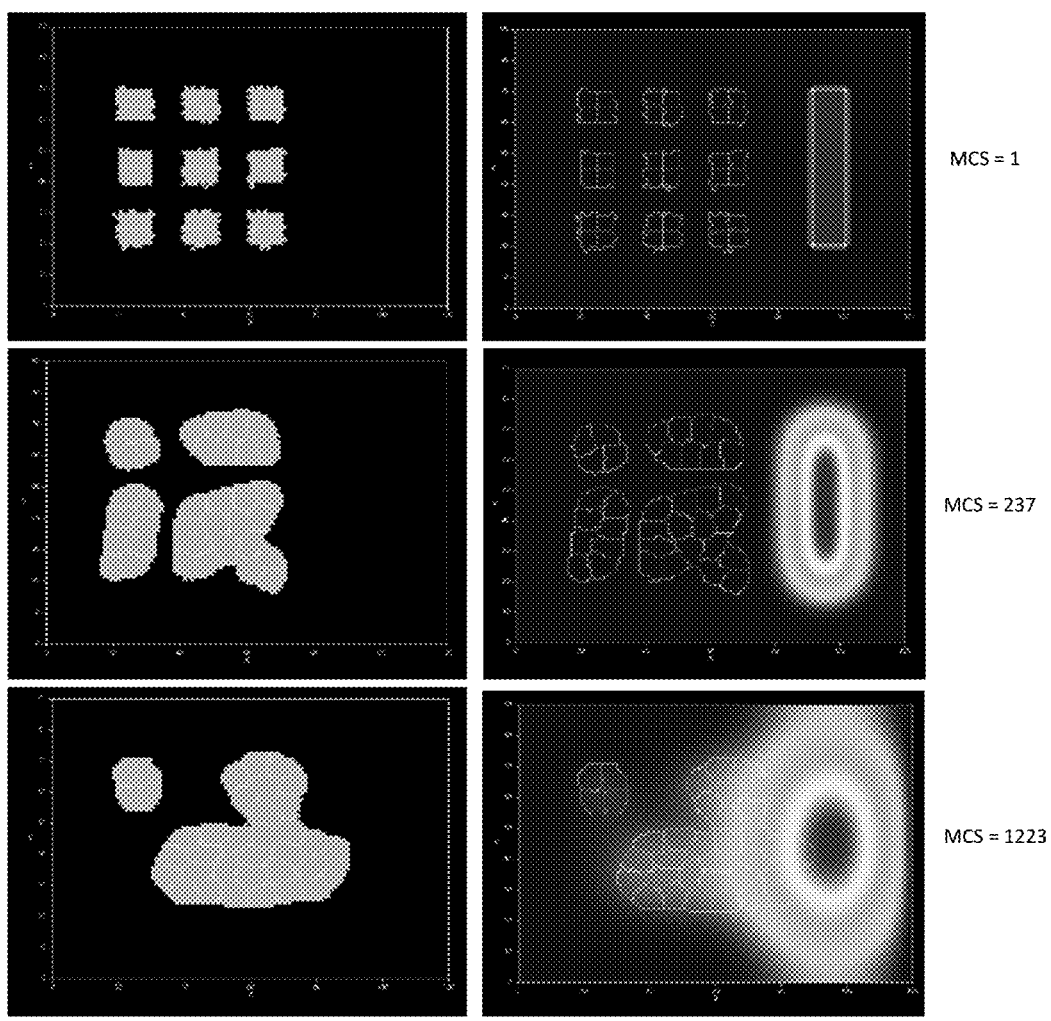
FIG. 5 depicts CompuCell 3D simulation results at different intervals of Monte Carlo Steps.

The simulations allow for the observance of how the vasculature structure is created and also enable their comparison to the interactions at the experimental level in the TrophoWell™. Through a series of iterations between the practical and theoretical observations, several aspects of experimental tissue engineering can be optimized, making TrophoWell™ usable for patient-individualized applications. This model allows for the assembly of information applicable to various experimental length scales and time scales of interactions FIG. 5 illustrates cell behaviors at different Monte Carlo Steps (MCS). The initial condition of the model contains four small aggregates of HUVEC cells and external VEGF supplied at a local secretion field. In the TrophoWell™, HUVEC cells in media and VEGF will be supplied from inlets in a similar manner and diffusion will spread out their clutter locations. Simulation results showed cells and growth factors diffused in the gel matrix. With time, they merge and respond to the VEGF with expected chemotactic behavior.

Figure 8A:
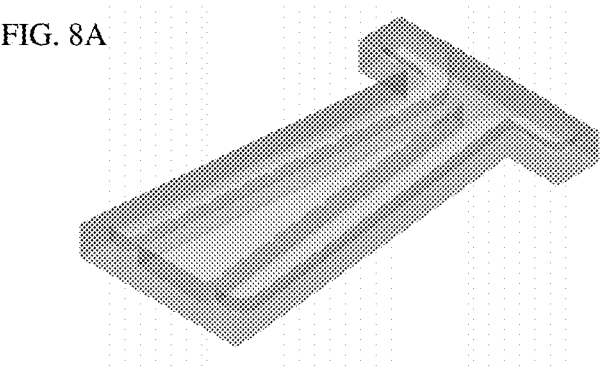
FIG. 8A shows a cross sectional view of a triangular chamber lined with two corridors distributing different substances periodically at different distances of reaction.
Figure 8B:
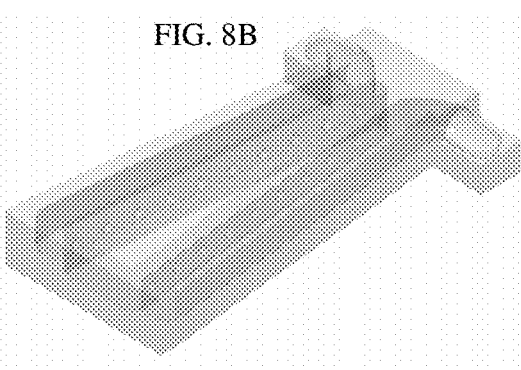
FIG. 8B illustrates a 3D-view of a triangular chamber lined with two corridors distributing different substances periodically at different distances.
Figure 9:
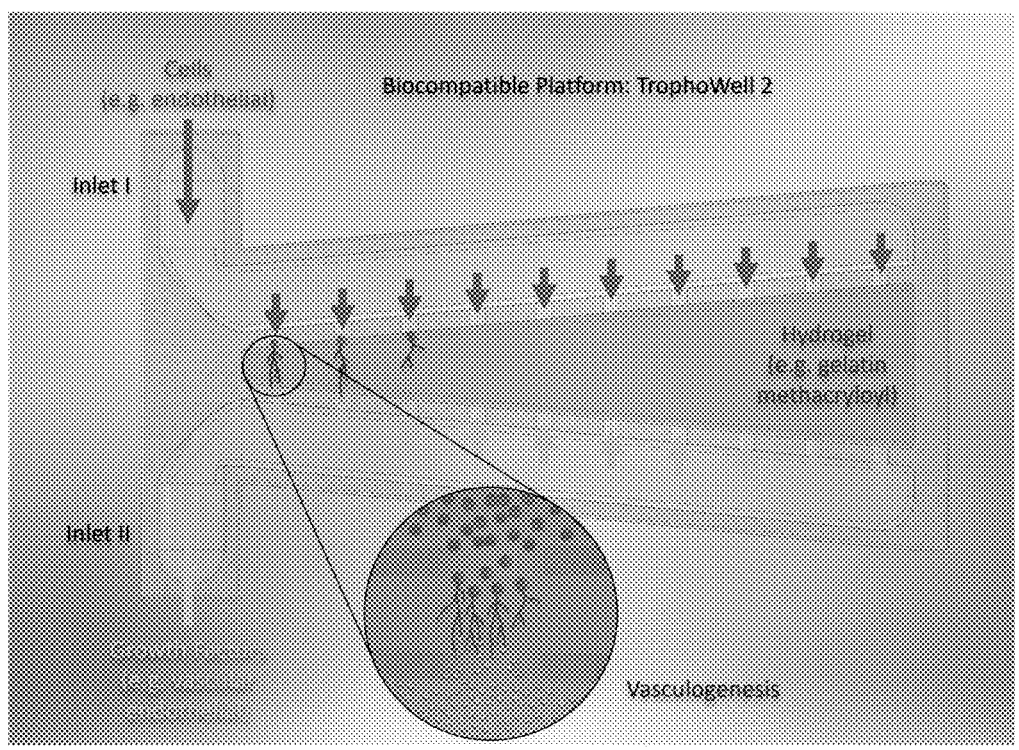
FIG. 9 shows a vasculogenesis analysis with TrophoWell™.
Figure 10A:
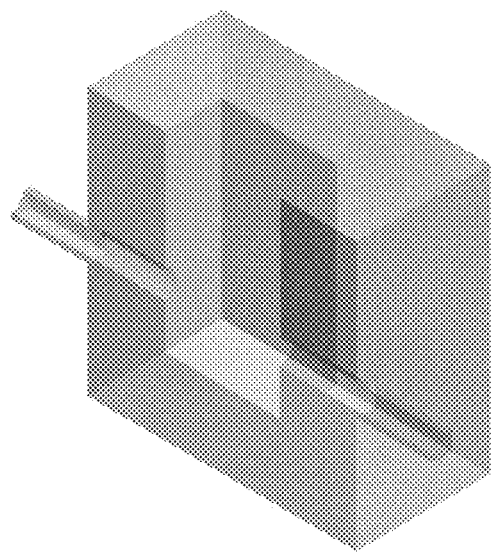
FIG. 10A illustrates a cross-sectional view of a cubic chamber with two inlets.
Figure 10B:
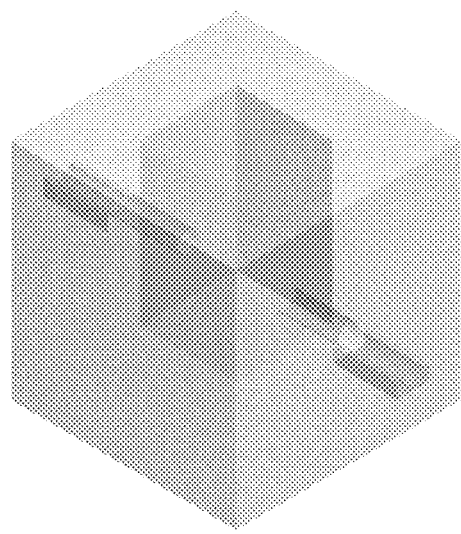
FIG. 10B illustrates a 3D view of a cubic chamber with two inlets.
Figure 11A:
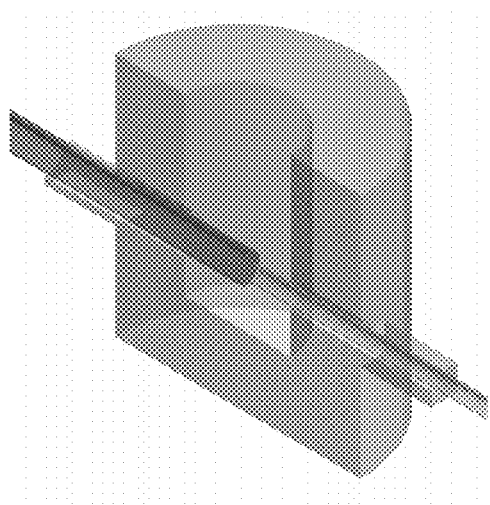
FIG. 11A shows a cross sectional view of a cylindrical chamber with two adjustable inlets.
Figure 11B:
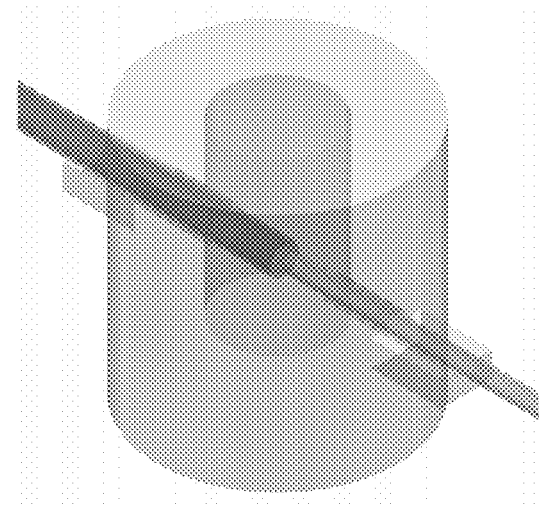
FIG. 11B illustrates a 3D view of a cylindrical chamber with two adjustable inlets.
Figure 12A:
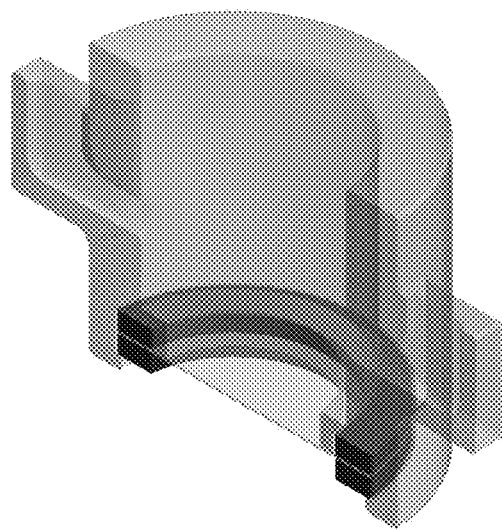
FIG. 12A depicts a cross sectional view of a cylindrical chamber with two fixed inlets and rubber O-rings.
Figure 12B:
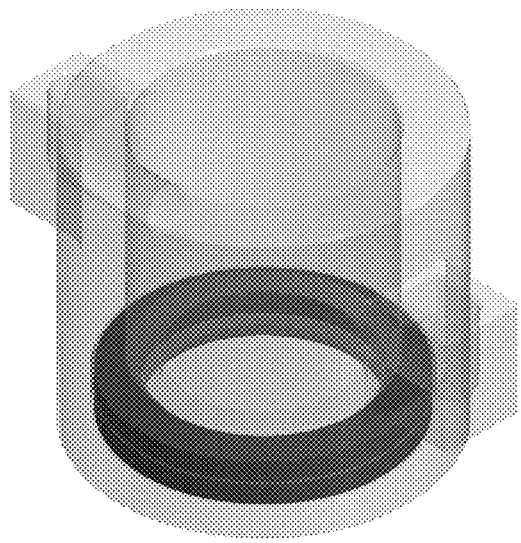
FIG. 12B shows a 3D view of a cylindrical chamber with two fixed inlets and rubber O-rings.
Figure 13A:
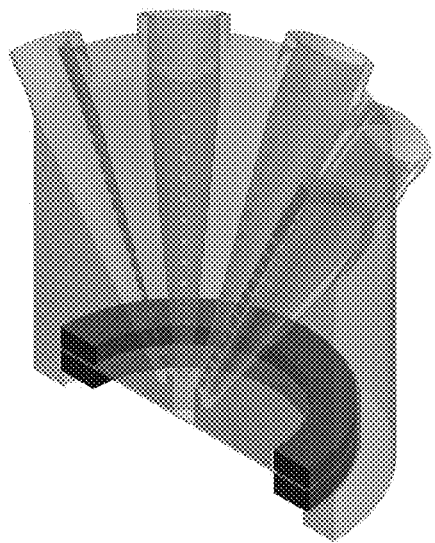
FIG. 13A shows a cross sectional view of a downward conical chamber with eight inlets.
Figure 13B:
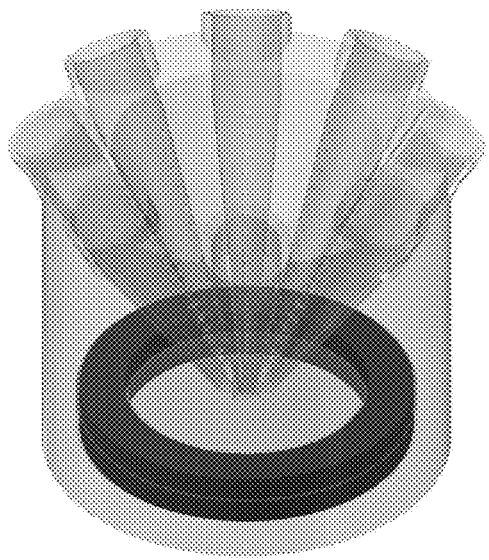
FIG. 13B illustrates 3D view of a downward conical chamber with eight inlets.
Figure 14A:
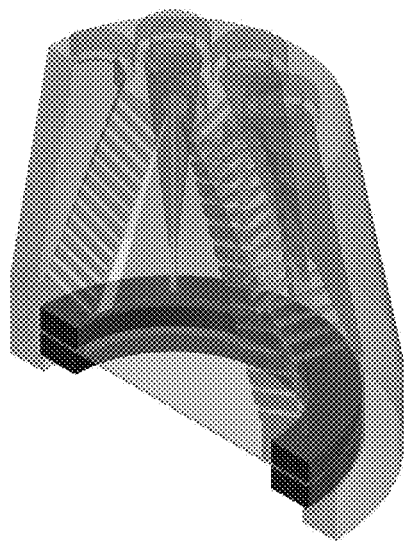
FIG. 14A shows a cross sectional view of an upward conical chamber with eight inlets.
Figure 14B:
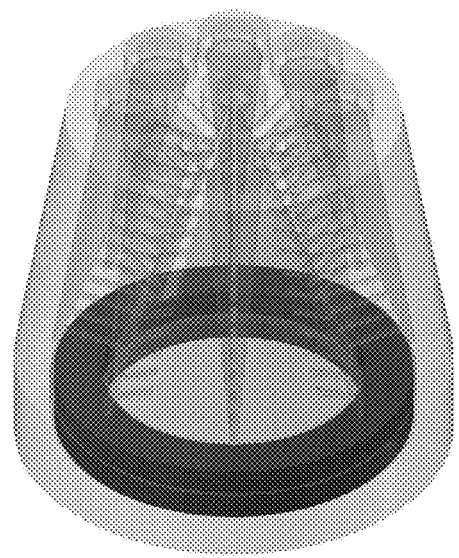
FIG. 14B depicts a 3D view of an upward conical chamber with eight inlets.

FIGS. 8-14 illustrate the different embodiments of the Trophowell™. FIGS. 8-9 illustrates a triangular chamber lined with two corridors distributing different substances periodically at different distances of reaction. FIG. 10 illustrates a cubic chamber with two inlets. FIG. 11 illustrates a cylindrical chamber with two adjustable inlets, where capillary tubes can be pushed further in and out of the chamber to gauge the appropriate distance of diffusion-reaction between the two. FIG. 12 illustrates a cylindrical chamber with two fixed inlets and rubber O-rings to hold a glass slide in place for ideal optical visualization of the internal reactions of the chamber. FIG. 13 illustrates a downward conical chamber with eight inlets distributing different substances periodically at different distances of reaction. FIG. 14 illustrated an upward conical chamber with eight inlets distributing different substances periodically at different distances of reaction.

In the embodiment illustrated in FIGS. 8 and 9, the TrophoWell™ has two inlets to introduce cells and growth factors. According to the literature, the distance between cells and growth factor can be a maximum of 200 μm in order to enable the cells to build a functional vascular tree[21]. This is because the cells must be able to reach the nutrients and growth factors to create a vascular tree. The central chamber contains the hydrogel in the Trophowell™ as illustrated in FIG. 9. The structure contains two corridors lined with periodic outlets communicating with the hydrogel environment. The distance between opposing outlets from the two different corridors increases to test the limit of diffusion and cellular-level interactions. As illustrated in this embodiment, it is possible to analyze the optimum dimensions for vascularization pathway and compare it to modelling and simulation results. The cells in growth media flow through inlet I, as illustrated in FIG. 9. Growth factor simulating vasculature formation is flown through inlet II.

The cells flow through the corridors and go through the periodic outlets (shown via blue arrows) into the hydrogel. Depending on the distance between two opposing outlets, vasculogenesis may or may not occur.

TrophoWell™ is an alternative platform for testing new drugs at early-stage experimentation. This alternative platform can dramatically obviate excess animal usage and their maintenance during new drug development. TrophoWell™ can be used as a quality control measure in early-stage experiments that designate whether the treatment is appropriate and optimized for sequential animal and clinical testing. Considering the excessive amount of animal deaths due to failed experiments, TrophoWell™ can play a critical role to decrease such waste. In some cases, it may even replace the animal studies if the tissue engineering is a more accurate model for the concerned research.

Furthermore, the TrophoWell™ is a test platform which has a high capability to be used for a variety of experiments. Autologous cells may be analyzed to study the immune response to a specific drug and also the harmful side-effects of those drugs. Additionally, an accurate dosage of this specific drug per patient may be analyzed again with this platform. Thus, this platform offers a beneficial way to solve the most important drawbacks of personalized medicine. This is because this platform provides equal accessibility for each patient. TrophoWell™ is a cost-effective alternative for cell analysis. It consists of two capillary tubes and a reaction pool which is fabricated by a biocompatible dental resin. Since a small-scale device can be developed with a volume approximately 100 mm$^3$. Another important advantage of the TrophoWell™ is the ease of implementation in clinical spaces, and the quick usage of such device.

Methods and Materials
Simulation

The geometric nature of the TrophoWell™, renders itself to modelling done by using the same CAD file that was used for 3D printing through software such as COMSOL® or to simulations by precision software. The behavior of HUVEC cells in creating a vascular network is modelled using CompuCell3D®, which is a lattice-based modeling platform developed by Dr. James A. Glazier and his colleagues. CompuCell3D® uses two famous biocomputational methods called Glazier-Graner-Hogeweg (GGH) and Cellular Potts Model.

Manufacturing of the TrophoWell™

The stereolithography technique is used to print a structure from a viscous liquid resin which solidifies by UV light. This technique enables the printing of different geometries for the design. The TrophoWell™ design is created on a CAD design platform by Autodesk Inventor. With this approach, a variety of geometrical shapes may be implemented into the design depending on the application selected. The stereolithography technique is used to 3D print TrophoWell™ using biocompatible Dental LT resin which is a commercial resin. Form 2 which is a stereolithographic 3D printer and is used to print TrophoWell™ using Dental LT resin.

A CAD design is uploaded onto PreForm 3D, the software program of the Form 2 3D printer. Support structures are generated to preserve the internal structures as designed. The amount of TrophoWell™ and the volume of the design is limited by the area of the build platform where the TrophoWell™ structure is built. For the cylindrical TrophoWell™ design, 24 of them can fit comfortably within the limitations of the build platform area. This print takes an average of 2 hours to print which is very fast for the production of a functional biomedical device.

The printing process is simple since the printing parameters are selected through the PreForm software, requiring no control during the printing process other than regular oversight. After the printing process is done, TrophoWell™ is taken off from the build platform using a spatula without causing any damage to the design or the platform. Since the resin is highly viscous, surface and the internal design of the TrophoWell™ may have excess amount of resin. Isopropanol alcohol can be used to soften the resin and remove both print and residual resin in a clean manner.

In the next step, the TrophoWell™ is immersed in a bath of IPA at room temperature for 5 minutes to eliminate all residual resin remaining in the internal walls of the structure. 5 minutes is appropriate for small designs, and large designs may need more time, but no more than 20 minutes maybe needed. A longer immersion time may cause the print to crack during the UV curing step. If the printed design still has sticky locations and the 5 minutes wash was not sufficient, a second 5 minutes second wash is recommended. After the TrophoWell™ is taken out from the IPA bath, the design is air-dried to let the IPA evaporate for at least one hour. When the TrophoWell™ is dry and all the excess resin is taken out, it is cured by ultraviolet light. The automated UV curing device is used for this purpose. UV curing time and temperature are specific for each resin and provided on the Formlabs website. For Dental LT resin, the recommended curing time is 20 minutes at 80° C.

UV curing process is the last step of the TrophoWell™ manufacturing process. After the design is successfully printed, capillary tubes (outer diameters are 1.8 and 1.0) are assembled into the inlets and outlets of the TrophoWell™ to supply biological substances needed for the variety of applications. Microvascularization application requires a specific distance between the endothelial cells and vascular endothelial cells to form a successful vasculature, therefore, the distance between capillary tubes are assigned in range of 200 micron to 500 micron. The empty area inside of TrophoWell™ is filled with a gelatin-based biomaterial to resemble an extracellular matrix environment for the cells.

The size of the TrophoWell™ is limited by the volume capabilities of the built platform of the 3D printer. However, the smaller the TrophoWell™ design is, the greater the number of TrophoWell™ can be printed at the same time.

Experimental Design: Vascularization

Vascularization experiment is conducted in three main steps. First, the TrophoWell™ is printed using the Form 2 stereolithography printer with dental biocompatible resin. Second, human umbilical vein endothelial cells (HUVEC) are cultured with their appropriate cell culture kit. The HUVEC cells are dyed with a fluorescent dye and differentiated. HUVEC cells are cultured, differentiated, and dyed to evaluate the cell behaviors and allow for tracking. In preparation for the third step, the biological experiment, the TrophoWell™ is filled with a structural gelatin-based material, the hydrogel to provide an environment resembling the cell's native ECM. In the third step, syringe pumps are used to supply fluid flow of growth factors while peristaltic pumps are used to transfer HUVEC cells in media from bioreactors, where they are differentiated, to the inlets of the TrophoWell™. Such tools are also used to control the fluid flow with high precision.

REFERENCES

[1] Berthiaume, François, Timothy J. Maguire, and Martin L. Yarmush. "*Tissue Engineering and Regenerative Medicine: History, Progress, and Challenges.*" Annual Review of Chemical and Biomolecular Engineering 2, pp. 403-430 (2011). URL: https://www.annualreviews.org/doi/pdf/10.1146/annurev-chembioeng-061010-114257
[2] Christian Frantz, Kathleen M. Stewart, and Valerie M. Weaver. "*The extracellular matrix at a glance.*" Journal of Cell Science 123, pp. 4195-4200 (2010). URL: http://jcs.biologists.org/content/joces/123/24/4195.full.pdf
[3] Clear dental resin by Formlabs: https://support.formlabs.com/s/article/Printing-Splints-with-Dental-LT-Clear-Resin?language=en_US
[4] Autoclavable surgical resin by Formlabs: https://support.formlabs.com/s/article/Using-Dental-SG-Resin?language=en_US
[5] Park, Kyung Min, Sharon Gerecht. "Harnessing developmental processes for vascular engineering and regeneration." Development for Advances in Developmental Biology and Stem Cells 141.14, pp. 2760-2769 (2014). URL: http://dev.biologists.org/content/141/14/2760
[6] FAMES Lab Website: https://fames.indiana.edu/
[7] Formlabs's Form 2: https://formlabs.com/fr/3d-printers/form-2/
[8] CELLINK's Bio X: https://cellink.com/bioprinter/?tab=BIO %20X
[9] Online article, US statistics of laboratory animals used in research: https://speakingofresearch.com/facts/statistics/ Regulation of Animal Research (Welfare Act): https://www.ncbi.nlm.nih.gov/books/NBK24650/
[10] Charan, Jaykaran, and N. D. Kantharia. "How to calculate sample size in animal studies?" Journal of Pharmacology 4.4, pp. 303-306 (2013). URL: http://www.jpharmacol.com/temp/JPharmacolPharmacother44303-4407023_121430.pdf
[11] Statement given on an academic forum discussion "How do you establish the minimal number of animals to test to get statistically significant data?", after publishing his paper providing a typical example of a rodent animal study protocol: Bekusova, Victoriia, Vasily Patsanovskii, Alexander D. Nozdrachev, Alexandr P. Trashkov, Margarita R. Artemenko, and Vladimir N Anisimov. "*Metformin prevents hormonal and metabolic disturbances and 1,2-dimethylhydrazine-induced colon carcinogenesis in non-diabetic rats.*" Cancer Biology and Medicine 14.1 (2017). URL: http://www.cancerbiomed.org/index.php/cocr/article/view/1013
[12] Lovell-Badge, Robin. "*Nine out of ten statistics are taken out of context.*" Understanding Animal Research (2013). URL: http://www.understandinganimalresearch.org.uk/files/3314/1041/0671/nine-out-of-ten-stat.pdf
[13] Image source: COSMOS: "*Lab mice make poor models for real-world immune systems.*"
[14] Fauber, John. "*Kalydeco: A Price Too High to Pay?*" MedPage Today (2013). URL: https://www.medpagetoday.com/pulmonology/cysticfibrosis/42018
[15] Kantarjian, Hagop. "*The Arrival of Generic Imatinib Into the U.S. Market: An Educational Event.*" The ASCO Post (2016). URL: http://www.ascopost.com/issues/may-25-2016/the-arrival-of-generic-imatinib-into-the-us-market-an-educational-event/
[16] Genetics Home Reference: "*What Is the Precision Medicine Initiative?*" URL: https://ghr.nlm.nih.gov/primer/precisionmedicine/initiative
[17] Image source: Global Business Outsource: "Population diversity as a crucial source of long-term prosperity in the US."[3] FAMES Lab Website: https://fames.indiana.edu/
[18] National Institute of Health All of Us Research Program: "*The All of Us Consent Process.*" URL: https://allofus.nih.gov/about/protocol/all-us-consent-process#undefined

What is claimed is:

1. A method of testing drugs, the method comprising:
providing a device,
said device comprising:
(i) a plurality of device walls that define an interior enclosure, said interior enclosure further comprising a hydrogel located within said device walls;
(ii) a first and second capillary tube, wherein the open distal ends of said first and second capillaries extend into said interior enclosure and the first and second capillaries are in fluid communication with said interior enclosure, further wherein said first and second capillaries are configured to allow a biologically active substance and/or cells to transit said capillaries and be delivered to said interior enclosure, and said first and second capillaries are configured to be independently movable relative to said device walls to alter the distance between the distal ends of the first and second capillary relative to each other; and
(iii) an optical port that allows for observations under microscope;
flowing cells through said first capillary and into said interior enclosure,
flowing a biologically active substance through said second capillary,
wherein the distance separating the distal ends of the respective first and second capillaries is adjusted based on the diffusion coefficient of the biologically active substance flowing through the second capillary, the hydrogel contained in the interior enclosure, and the cells flowing through the first capillary.

2. The method of claim 1, wherein the interior enclosure allows for imaging of the cells within the hydrogel.

3. The method of claim 1, wherein the first and second capillaries have different diameters.

4. The method of claim 1, wherein said device comprises additional capillaries in fluid communication with the interior enclosure, and a biologically active substance is delivered to the interior enclosure through more than one of said secondary capillary and said additional capillaries.

5. The method of claim 1, wherein said device comprises additional capillaries in fluid communication with the interior enclosure, and more than one biologically active substance is delivered to the interior enclosure separately through more than one of said secondary capillary and said additional capillaries.

6. The method of claim 1, wherein HUVECs are delivered to the interior enclosure through the first capillary, VEGF is delivered to the interior enclosure through the second capillary, and microvaculature growth is observed in the interior enclosure via an optical guide formed in a wall of the device.

* * * * *